(12) United States Patent
Schreder et al.

(10) Patent No.: US 8,008,349 B2
(45) Date of Patent: *Aug. 30, 2011

(54) STABLE PHARMACEUTICAL PREPARATION COMPRISING LEVOTHYROXINE SODIUM, GELATIN AND FILLERS AND WHICH IS FREE OF ORGANIC SOLVENT RESIDUES

(75) Inventors: Sven Schreder, Heidelberg (DE); Marion Nischwitz, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 1892 days.

This patent is subject to a terminal disclaimer.

(21) Appl. No.: 10/661,588

(22) Filed: Sep. 15, 2003

(65) Prior Publication Data

US 2004/0063611 A1 Apr. 1, 2004

Related U.S. Application Data

(62) Division of application No. 09/700,421, filed as application No. PCT/EP99/03087 on May 5, 1999, now Pat. No. 6,646,007.

(30) Foreign Application Priority Data

May 15, 1998 (DE) .................................. 198 21 625

(51) Int. Cl.
*A61K 31/198* (2006.01)
(52) U.S. Cl. ...................................................... 514/567
(58) Field of Classification Search .................... 514/567
See application file for complete search history.

(56) References Cited

U.S. PATENT DOCUMENTS

| 3,621,098 A | 11/1971 | Prange et al. | |
|---|---|---|---|
| 3,808,332 A | 4/1974 | Reynolds | |
| 5,225,204 A | 7/1993 | Papadimitrou et al. | |
| 5,955,105 A * | 9/1999 | Mitra et al. | 424/464 |
| 6,491,946 B1 * | 12/2002 | Schreder et al. | 424/465 |
| 2005/0003491 A1 * | 1/2005 | Jacobs et al. | 435/69.1 |

FOREIGN PATENT DOCUMENTS

| DE | 195 41 128 | | 4/1997 |
|---|---|---|---|
| GB | 1180574 | | 2/1970 |
| GB | 1296510 | | 11/1972 |
| WO | WO 93/04691 | * | 3/1993 |

OTHER PUBLICATIONS

Remington's Pharmaceutical Sciences (15th edition), Mack Publishing Company, PA (1975), p. 1578.*
Kokil et al., AAPS PharmSciTech (2004), 5(3), pp. 1-5.*
Derwent World Patent Index AN 97-527238 & CN 1 126 589 (Jul. 17, 1996).

* cited by examiner

*Primary Examiner* — Phyllis G. Spivack
(74) *Attorney, Agent, or Firm* — Millen, White, Zelano & Branigan, P.C.

(57) ABSTRACT

The invention relates to a pharmaceutical preparation comprising levothyroxine sodium, gelatine and fillers, which is free of organic solvent residues.

14 Claims, No Drawings

STABLE PHARMACEUTICAL PREPARATION COMPRISING LEVOTHYROXINE SODIUM, GELATIN AND FILLERS AND WHICH IS FREE OF ORGANIC SOLVENT RESIDUES

The invention relates to a novel stable pharmaceutical preparation comprising levothyroxine sodium, gelatine and fillers and which is free of organic solvent residues.

This novel preparation has an improved stability and can be used as a thyroid hormone preparation.

This novel preparation furthermore has an improved release of active compound in vitro.

The invention was based on the object of making available novel medicaments in the form of pharmaceutical preparations, which have better properties than known medicaments used for the same purposes.

In the Federal Register Vol. 62, No. 15, Aug. 14, 1997; page 43535, the Department of Health and Human. Services, Food and Drug Administration, published the facts that the products available on the U.S. market which comprise levothyroxine sodium and are orally administered have stability problems and therefore must be present in an up to 20% excess dose and that manufacturers must develop appropriate novel administration forms. The requirements on in-vitro release for levothyroxine Na tablets have furthermore been increased. The monograph draft version of the Pharmacopeial Forum (Pharm. Preview, 1995, 21, 1459-1461) proposes, in addition to the valid Test 1 (phosphate buffer pH 7.4, in 80 minutes >55%) to approve Test 2 (water in 45 minutes >70%).

This object was achieved by the discovery of the novel preparation.

Thyroxine-containing preparations with other additives such as glycine, a carbohydrate and an inorganic salt are disclosed in WO 97 17 951.

Another thyroxine preparation stabilized with thiosulfate is described in DE 195 41 128.

A combination preparation comprising levothyroxine sodium and potassium iodide is known from U.S. Pat. No. 5,635,209. Another thyroxine-containing formulation which contains thyroxine/cyclodextrin complexes is described in WO 97 19 703.

In addition to levothyroxine sodium, the pharmaceutical formulation according to the invention can also contain liothyronine sodium.

The invention preferably relates to a pharmaceutical preparation as described, characterized in that it contains 5 to 400 μg, preferably 10 to 300 μg, in particular 25 to 300 μg, of levothyroxine sodium.

The invention furthermore preferably relates to a pharmaceutical preparation as described, characterized in that it contains levothyroxine sodium micronized with a particle size of between 5 μm and 25 μm.

The invention furthermore preferably relates to a pharmaceutical preparation as described, characterized in that it contains fillers selected from the group consisting of lactose and/or maize starch and/or microcrystalline cellulose.

A particularly preferred pharmaceutical preparation is one characterized in that it is a solid preparation in the form of tablets.

Particularly preferred embodiments contain 25, 50, 75, 100, 125, 150, 175 or 200 μg of levothyroxine sodium.

The active compound(s) is/are sensitive to light, heat and oxygen. On account of this known instability, the active compound is in an excess dose of up to 5% in the formulations.

The preparation according to the invention has a surprising stability when gelatine is used as a binder.

If this is replaced by another customary binder such as Methocel, even at the start of the stability investigations a decline in the active compound content is detected and furthermore the sum of the by-products is increased.

If, for example, the starting value of active compound is determined in a 100 μg batch in which gelatine has been replaced by Methocel, instead of the 105% to be expected only 100.48% is found.

Stability investigations show that the tablets according to the invention which contain levothyroxine sodium are stable for at least 2 years if they are stored at temperatures below 30° C.

Furthermore, the release of the active compound levothyroxine sodium is surprisingly favoured if the active compound is employed in micronized form. Levothyroxine sodium is customarily very sparingly soluble both in water and also in ethanol. With a particle size between 5 μm and 25 μm (to 95%), however, a release of the active compound takes place in Test 1 to >90% (phosphate buffer) and in Test 2 to >80% (water).

Surprisingly, the composition according to the invention can also be prepared without the use of organic solvents. If the water used in the process according to the invention is replaced by an organic solvent such as, for example, methanol, a decline in the content of levothyroxine sodium by 10% is moreover seen in test batches after 1 year at a storage temperature of 25° C. and 60% rel. humidity.

Suitable fillers for the pharmaceutical preparation according to the invention are preferably lactose, maize starch and/or microcrystalline cellulose, both as individual fillers and in combinations with one another. Particularly preferred pharmaceutical preparations, as described, contain maize starch and lactose.

The invention also relates to a process for the production of a pharmaceutical preparation comprising levothyroxine sodium and optionally liothyronine sodium, characterized in that levothyroxine sodium and optionally liothyronine sodium, which is/are present in suspended form in aqueous gelatine solution, are sprayed onto the filler(s) in a fluidized bed granulation, then a disintegrant and lubricant are admixed and the mixture is compressed to give tablets.

The invention further relates to a process as described, characterized in that the disintegrant used is croscarmellose sodium and the lubricant used is magnesium stearate.

Further excipients or auxiliaries can be added, such as, for example, binding agents, antioxidants, colorants, lubricants, sweeteners and/or aromatic substances.

Preferred glidants or lubricants are, for example, talc, starch, magnesium and calcium stearate, boric acid, paraffin, cocoa butter, macrogol, leucine or sodium benzoate; magnesium stearate is very particularly preferred.

The following examples relate to the production and the composition of the pharmaceutical preparation according to the invention:

EXAMPLE 1

The following amounts are needed in order to prepare, for example, 2 million tablets:

| Levothyroxine 100 μg | |
| --- | --- |
| Ingredient | Amount [kg] |
| Levothyroxine sodium* | 0.210 |
| Lactose monohydrate | 131.80 |
| Maize starch | 50.00 |
| Gelatine | 10.00 |
| Croscarmellose sodium | 7.00 |
| Magnesium stearate | 1.00 |
| Water, purified** | 56.66 |

*A 5% excess dose of levothyroxine sodium was additionally included.
**The water is removed again by drying.

Preparation:

1. Gelatine is dissolved in about 90% of water at a temperature from 80 to 100° C.

Levothyroxine sodium is suspended in about 10% of the water at room temperature.

The suspension is then added to the gelatine solution at 50° C. (±5° C). The temperature of the suspension thus obtained (=granulation liquid) is 45 to 50° C.

2. Lactose and maize starch are placed in a fluidized bed granulator. The granulation liquid is sprayed over the powder. The temperature of the granulation liquid is kept between 40 and 50° C. during the spraying process. During the granulation, the temperature at the inlet is kept at approximately 70° C. (±5° C.) and the temperature at the outlet is kept between 20 and 40° C. The spraying pressure is between 3 and 5 bar. After spraying, the granules are dried until a temperature of approximately 40° C. is reached at the outlet.

The dry granules are then screened (1 mm) according to known methods (=mixture a).

Croscarmellose sodium and magnesium stearate are correspondingly screened. The components are then mixed with one another for 10 minutes together with mixture a in a drum mixer.

The press-ready mixture is then compressed to give tablets.

EXAMPLE 2

Composition of a 100 mg (±3 mg) tablet which contains 100 μg of levothyroxine sodium:

| | | |
|---|---|---|
| | Levothyroxine sodium | 0.100 mg |
| | Lactose monohydrate | 65.90 mg |
| | Maize starch | 25.00 mg |
| | Gelatine | 5.00 mg |
| | Croscarmnellose sodium | 3.50 mg |
| | Magnesium stearate | 0.50 mg |
| | | 100.00 mg |

Levothyroxine sodium is to be present in an around 5% excess dose.

EXAMPLE 3

Composition of a 100 mg (±3 mg) tablet which contains 100 μg of levothyroxine sodium:

| | | |
|---|---|---|
| | Levothyroxine sodium | 0.100 mg |
| | Liothyronine sodium | 0.020 mg |
| | Lactose monohydrate | 65.88 mg |
| | Maize starch | 25.00 mg |
| | Gelatine | 5.00 mg |
| | Croscarmellose sodium | 3.50 mg |
| | Magnesium stearate | 0.50 mg |
| | | 100.00 mg |

Levothyroxine sodium is to be present in an around 5% excess dose.

The invention claimed is:

1. A pharmaceutical preparation comprising active compound, 5 mg gelatin as a binder and fillers and which is free of organic solvent, wherein the active compound is levo-thyroxine sodium, and which preparation is in tablet form.

2. The pharmaceutical preparation according to claim 1, containing 5 to 400 μg of levothyroxine.

3. The pharmaceutical preparation according to claim 1, containing levothyroxine sodium micronized with a particle size of between 5 μm and 25 μm.

4. The pharmaceutical preparation according to claim 1, wherein the filler is lactose, maize starch or microcrystalline cellulose.

5. A pharmaceutical preparation comprising levo-thyroxine sodium, 5 mg gelatin as a binder and fillers which is free of organic solvent and which is in solid form.

6. The pharmaceutical preparation according to claim 5, containing 5 to 400 μg of levothyroxine.

7. The pharmaceutical preparation according to claim 5, containing levothyroxine sodium micronized with a particle size of between 5 μm and 25 μm.

8. The pharmaceutical preparation according to claim 5, wherein the filler is lactose, maize starch or microcrystalline cellulose.

9. The pharmaceutical preparation according to claim 5, comprising levothyroxine sodium, lactose, starch, gelatin, croscarmellose sodium, and magnesium stearate.

10. The pharmaceutical preparation according to claim 9, further comprising liothyronine sodium.

11. A pharmaceutical preparation comprising active compound, 5 mg gelatin as a binder and fillers and which is free of organic solvent wherein the active compound consists essentially of levo-thyroxine sodium and liothyronine sodium, and which preparation is in solid form.

12. The pharmaceutical preparation according to claim 11, containing 5 to 400 μg of levothyroxine.

13. The pharmaceutical preparation according to claim 11, containing levothyroxine sodium micronized with a particle size of between 5 μm and 25 μm.

14. The pharmaceutical preparation according to claim 11, wherein the filler is lactose, maize starch or microcrystalline cellulose.

* * * * *